United States Patent [19]

Reiner

[11] Patent Number: 5,118,813
[45] Date of Patent: Jun. 2, 1992

[54] PROCESS FOR THE PREPARATION OF COMPOUNDS WITH ANTIULCER ACTION

[75] Inventor: Alberto Reiner, Cantu, Italy

[73] Assignee: Biote kfarma Srl, Rome, Italy

[21] Appl. No.: 597,282

[22] Filed: Oct. 16, 1990

Related U.S. Application Data

[63] Continuation of Ser. No. 420,712, Oct. 12, 1989, abandoned, which is a continuation of Ser. No. 255,195, filed as PCT/EP88/00041, Jan. 21, 1988, abandoned.

[30] Foreign Application Priority Data

Jan. 27, 1987 [IT] Italy .................... 19166 A/87

[51] Int. Cl.$^5$ .................. C07D 233/64; C07D 317/56
[52] U.S. Cl. .................................... 548/336; 549/435; 549/495; 549/440; 549/442; 548/342; 564/105
[58] Field of Search ............... 549/435, 492; 548/336, 548/342; 564/105

[56] References Cited

U.S. PATENT DOCUMENTS 4,157,340  6/1979  Crenshaw .................. 564/104

FOREIGN PATENT DOCUMENTS 0064869  11/1982  European Pat. Off. .
2386535  11/1978  France .
87/05902  10/1987  PCT Int'l Appl. .

OTHER PUBLICATIONS

Synthesis, No. 5, May 1985 (Stuttgart, DE), F. Moimas et al.; "A New Approac Approach To 1-Nitro-2, 2-Bis[Alkyl-or Aryl-Amino]Ehtylenes: A New Synthesis of Ranitidine", pp. 509–510, (whole document).
Chemical Abstracts, vol. 94, No. 7, 16 Feb. 1981, (Columbus, Ohio USA), see page 529, Abstract 46806m, & ES, A, 477817 (A. L. Palomo Coll et al.) 1 Jul. 1980.
Chemical Abstracts, vol. 105, No. 13, 29 Sep. 1986, (Columbus, Ohio U.S.A.), I. Kraemer et al.; "H$_2$-Antihistiminics. 29. Synthesis and H$_2$-Antagonist Activity of mono-and bis–functionalized hydrazines", see page 671, Abstract 11968p & Pharm. Ztg. 1985, 130(33), 2062–6.

Primary Examiner—Nicky Chan
Attorney, Agent, or Firm—Nikaido, Marmelstein, Murray & Oram

[57] ABSTRACT

For the preparation of compounds such as ranitidine, niperotidine and cimetidine a urea of the formula:

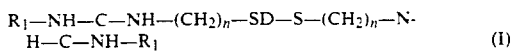

(I)

which is synthesized by reaction with a compound of formula

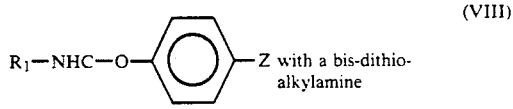

(VIII)

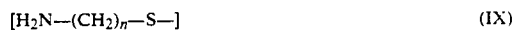

(IX)

is converted in a first stage into the corresponding bis-carbodiimide

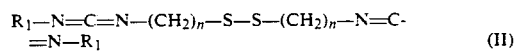

(II)

by reaction with triphenylphospine and bromine in the presence of a strong base and in a second stage the diimide thus obtained is reacted with nitromethane or a saline derivative of the cyanamide.

The product thus obtained is reduced at the disulfide bridge obtaining a compound of formula:

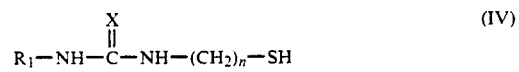

(IV)

which is reacted with:

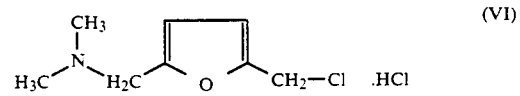

(VI)

or with

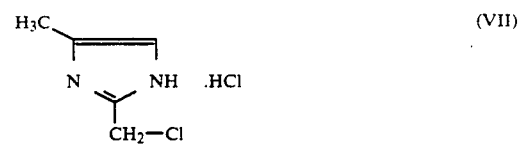

(VII)

to obtain ranitidine and niperotidine or cimetidine respectively depending on whether the first or the second of the described reactants is used.

29 Claims, No Drawings

PROCESS FOR THE PREPARATION OF COMPOUNDS WITH ANTIULCER ACTION

This application is a continuation of U.S. application Ser. No. 420,712 filed Oct. 12, 1989, now abandoned, which in turn is a continuation of U.S. application Ser. No. 255,195, filed as PCT/EP88/00041, Jan. 21, 1988, now abandoned.

The present invention relates to a process for the preparation of compounds with antiulcer action, specifically the compounds having the following general formula:

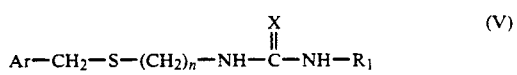

wherein $R_1$ represents hydrogen, alkyl, alkyl substituted with a single or substituted aromatic ring or with a single or substituted heterocyclic ring, Ar represents a single or substituted aromatic ring or heterocycle, $n = 1, 2, 3, 4, 5$ or $6$ and X represents $CH-NO_2$, $S, N-C|N$. Compounds covered by the above general formula and well known include:

(1) ranitidine, for which in the above formula:

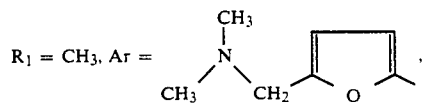

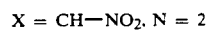

(2) niperotidine, for which:

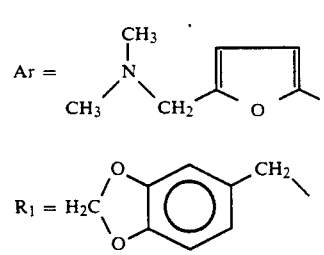

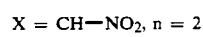

(3) cimetidine, for which:

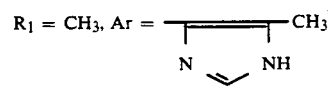

The therapeutic importance of the compounds in question makes any improvement in the process and/or yield of extreme interest.

The primary object of the present invention is to perfect a synthesis method for the compounds of the general formula (V). Said object is achieved by a process characterized by the stages:

a) reaction of a carbamate of the formula

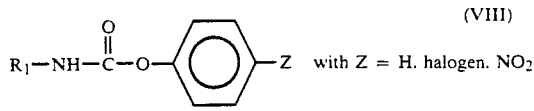

with a bisdithio-alkylamine of the formula:

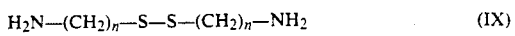

to obtain a urea of the formula

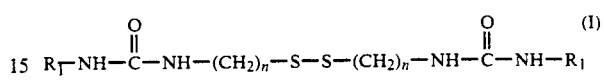

where $R_1$, n have the abovementioned meanings.

b) reaction of the urea of formula (I) with a compound capable of converting it into the corresponding bis-carbodiimide of the formula:

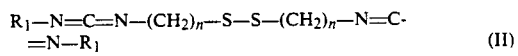

c) reaction of the carbodiimide of formula (II) with a compound selected from among nitromethane in the presence of a strong base and a saline derivative of the cyanamide to form the product of formula:

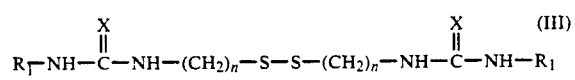

where $X = CH-NO_2$; $N-C \equiv N$ d) reaction of the compound of formula (III) with a compound with reduces the —S—S— group to obtain a compound of formula:

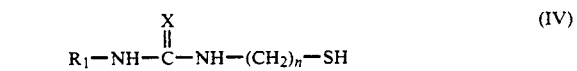

e) reaction of the compound of formula (IV) with a reactant of formula $AR-CH_2Cl$ to obtain the desired products of formula:

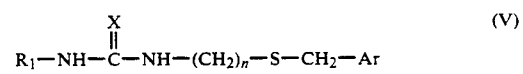

wherein $R_1$, X, Ar and n have the above meanings.

As appears from the above schematization the process in accordance with the invention makes it possible to obtain ranitidine, niperotidine or cimetidine directly depending on the meaning of $R_1$, Ar, X and n. From the following examples it can be readily seen that among the principal advantages of the present invention are to be counted process simplification and obtaining quantitative yields since the only obstacle to achievement of the latter advantage resides in the possible impurities of the reactants.

Now considering in detail the process of the present invention, synthesis of the urea of formula (I) (stage (a)) is carried out by reacting a carbamate of formula (VIII) dissolved in the solvent at a temperature of between approximately 40° C. and 50° C. with a compound of formula (IX) which has been freed from the hydrochloride by treatment with aqueous soda. The solvent must be capable of solubilizing the urea (I) and have a certain miscibility with water. Preferably this is pyridine and the aqueous soda solution utilized to liberate compound (IX) from the hydrochloride must be the minimun quantity possible since water would cause the urea (I) to precipitate again.

Concerning synthesis of compound II (stage (b)) it is first of all pointed out that the reactants capable of converting the urea (I) into the corresponding carbodiimide (II) are selected from among triphenylphosphine (Ph₃P), sulfuryl chloride (SO₂Cl₂) and thionyl chloride (SoCl₂). In the case of the triphenylphosphine, bromine must also be present and in all cases an acid acceptor, preferably an organic base, and still more preferably triethylamine, must be present. The reaction solvent is an aprotic solvent, preferably a chlorinated hydrocarbon such as dischloromethane, chloroform and others.

The reaction is carried out at low temperature and performed by introducing very slowly at a temperature on the order of 5° C. small portions of the urea (I) in a reactant already formed in the reactor starting from the compound selected from among triphenylphospine, thionyl chloride or sulfuryl chloride dissolved in the reaction solvent and having (if necessary) added bromine and the acid acceptor, specifically triethylamine.

The abovementioned reactant is also formed at low temperature, specifically below 0° C., and introducing slowly the different reactants. Once all the urea (I) has been added, the temperature is allowed to rise again spontaneously to room temperature and the reaction mixture is reacted while stirring for approximately 1-2 hours, after which the carbodiimide is isolated in a known manner.

Preferably the reactant into which the urea (I) is introduced is in excess of the stoichiometric quantity necessary for conversion. In the third reaction stage (c), when it is desired to prepare compound (III), the carbodiimide (II) in solution in a polar aprotic solvent, preferably dipolar such as dimethylformamide or dimethylsulfoxide, is added slowly at room temperature to a solution of nitromethane in the same solvent, prepared previously and containing a strong base such as for example sodium hydride.

Preferably the nitromethane is in molar excess of the carbodiimide. Once addition of the latter has been terminated, the reaction is completed in 15-20 hours at a temperature of approximately 40° C. with quantitative yields if the reactants are free of impurities.

If it is desired to prepare cimetidine, compound (II) is reacted with a saline derivative of cyanamide, preferably the sodium salt. In the fourth stage (d) of the synthesis, to the compounds of formula (III) are applied appropriate methods of reduction of the disulfide bridges known in the literature to obtain the compounds of formula (IV). They are preferably treated with for example sodium borohydride. The reaction solvent is a mixture of water and alcohol and preferably the alcohol is methanol, with an excess of alcohol.

In the fifth and last stage (e) the compounds of formula (IV) are reacted with a halogenide of formula (VI) if it is desired to obtain ranitidine and niperotidine and when the substituent X=CH—NO₂ or with a halogenide of formula (VIII) if it is desired to obtain cimetidine when the substituent X=N—C≡N.

In all cases the reaction is carried out in polar aprotic solvents and preferably dipolar ones such as dimethylformamide and dimethylsulfoxide. The reaction is carried out by introducing a solution of the halogenide (VI) or (VII) freed from the hydrochloride for treatement with an appropriate base, preferably sodium hydride, in a solution containing the sodium salt at the group SH obtained by reaction of the compounds (IV) with an appropriate base, preferably sodium hydride.

After this introduction the reaction mixture is brought to a temperature of approximately 70°-80° C. for 1-3 hours, then cooled to room temperature. Yields are quantitative if the reactants are free of impurities. The reaction mixture is concentrated in a vacuum to eliminate the solvent and then the raw product of formula (V) goes to the purification process. An example will now be given relative to the preparation of the niperotidine, it being understood that it is intended merely as illustrative and non limiting of the synthesis of which a general scheme is given.

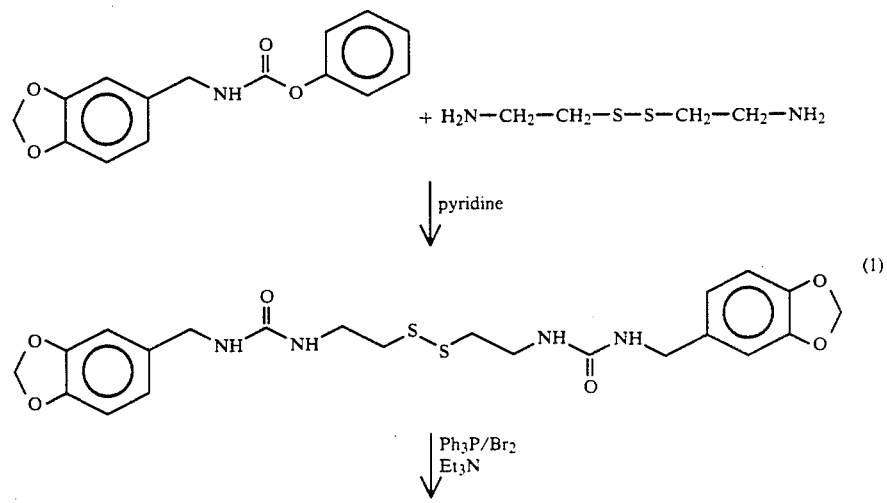

-continued

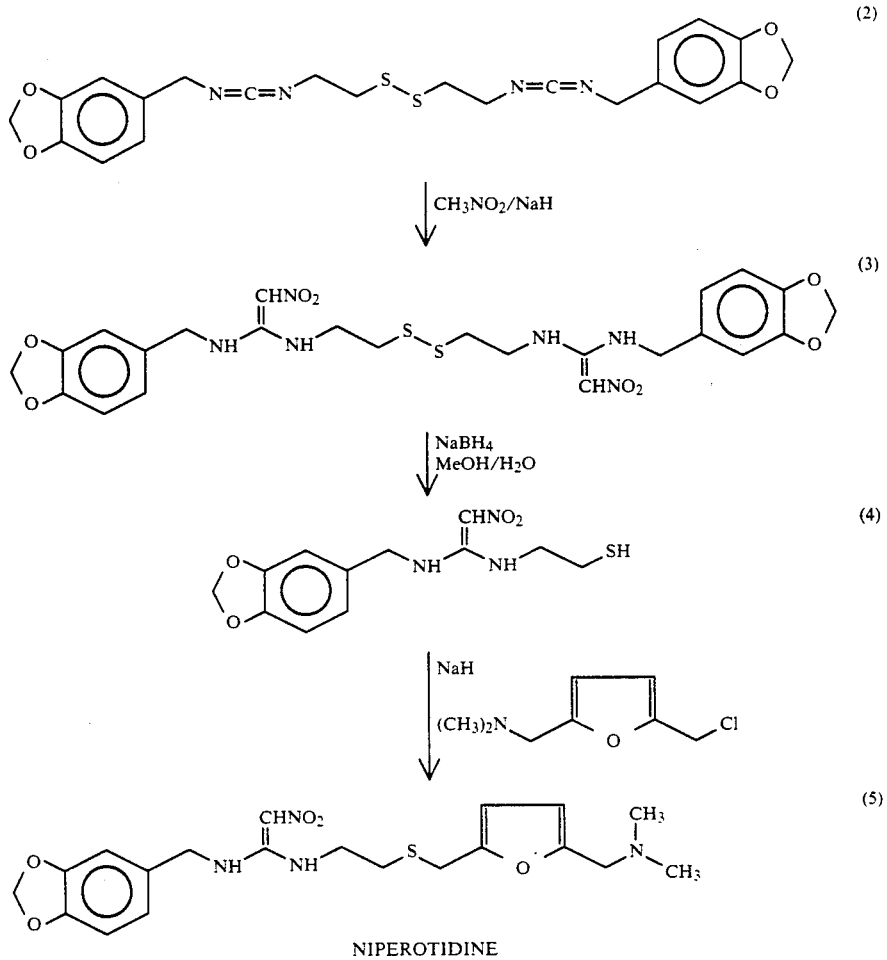

NIPEROTIDINE

EXAMPLE A

N,N'-di[N-(3,4-methylenedioxybenzyl)-carbamoyl]2,2'-dithiobisethanamine.

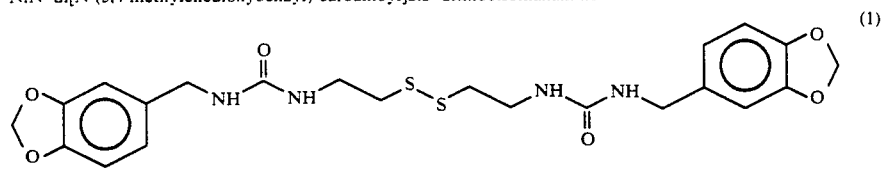

(1)

In a 500 ml 3-necked flask equipped with a stirring mechanism are placed 40 g of O-phenyl-N(3,4-methylenedioxybenzyl)-carbamate and 150 ml of pyridine. The reaction mixture is then brought to 45° C.

An aqueous solution (32 ml) containing 16.5 g of cystamine dihydrochloride and 5.88 g of sodium hydride is prepared separately. The aqueous solution is dropwise added to the pyridine solution and at the end the reaction mixture is heated to 90°–95° C. for approximately 20 hours. After cooling (with precipitation of a white substance) the reaction mixture is poured into 400 ml of water and after 2 hours of vigorous stirring the precipitated product is filtered and washed with water made acidic with acetic acid.

The product is repeatedly slurried in water and filtered to eliminate traces of pyridine, then it is poured into 60 ml of acetone to eliminate traces of phenol. It is filtered and vacuum dried at 60°–70° C. for 12 hours.

33 g of product are obtained with a yield of 88.7% and the melting point is 181°–183° C.

TLC control (Merck 5554); (eluent: ethyl acetate/n-hexane 1:1) Detector: UV, cerium phosphomolybdate. Rf=0.78

EXAMPLE B 1,1'-di/(3,4-methylenedioxybenzyl)carbodiimidyl/2,2'-dithiobis-ethane.

-continued

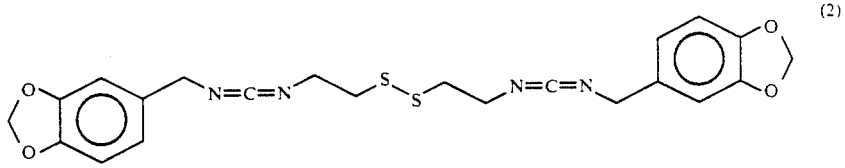

In a 250 ml 4-necked flask equipped with a stirring mechanism, a thermometer and a filling funnel are placed 80 ml of $CH_2Cl_2$ and 15.5 g of $Ph_3P$ until a clear colorless solution is obtained. The $Br_2$ (3 ml dissolved in 10 ml of $CH_2Cl_2$) is introduced very slowly at a temperature of between 0° C. and 10° C. The reaction mixture is stirred for further 30 minutes, then the product obtained in example A(10 g) is added in portions while holding the temperature between 0° C. and 5° C. At the end of the addition after approximately 1 hour the added product is completely solubilized. IR analysis is performed and a peak corresponding to the carbodiimide at 2120 cm$^{-1}$ is found. The reaction mixture of a dark yellow colour contains $Et_3NHBr$ is suspension. It is stirred again for 1 hour while allowing the temperature to rise again spontaneously to 20° C.

It is vacuum concentrated at a temperature below 30° C. to approximately half original volume. The $Et_3NHBr$ formed is filtered, then the filtered solution is concentrated to dryness to obtain an oily residue consisting of carbodiimide and $Ph_3PO$.

28.8 g of mixture are obtained. Theoretical yield of diimide + $Ph_3PO$ is 25.6 g.

EXAMPLE C

N,N'di[N-(3,4methylenedioxybenzyl)-1-amino-2-nitro-ethenyl]-2,2'-dithio-bis-ethanamine.

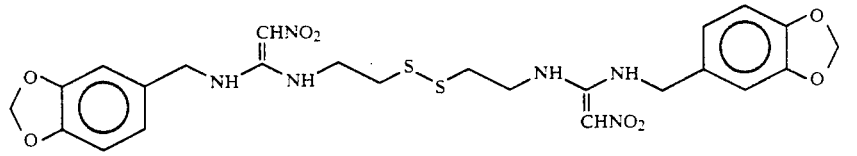

In a 250 ml 3-necked flask are placed 80 ml of dimethylsulfoxide and 1.8 g of sodium hydride. The mixture is stirred for 10 minutes and $CH_3NO_2$ (3.2 ml) is added.

After stirring at room temperature for 3 hours a yellow heterogeneous reaction mixture is obtained. The carbodiimide (9.2 g) previously obtained and dissolved in 20 ml of dimethylsulfoxide is introduced drop by drop at room temperature while stirring well. After completion of the addition (20 minutes) the mixture is brought to 35° C. and stirred for 15 hours. IR control checks are performed at 30 minute intervals for disappearance of the band corresponding to the carbodiimide, the peak of which disappears completely after 2 hours. The reaction mixture is vacuum concentrated to a small volume at a temperature of approximately 80° C. to obtain an oily residue which is purified by partitioning between chloroform and water (elimination of salts, removal of the residual DMSO and water soluble biproducts). The dried chloroform phase (anhydrous $Na_2SO_4$) is concentrated to dryness to obtain a brown solid residue which is dissolved in 100 ml of acetone and acidified with an excess of acetic acid.

After filtration of the precipitate formed, 5.7 g (47% yield) of a crystalline product (3) are obtained.

TLC control (Merck, eluent: ethyl acetate/methanol/$NH_4OH$ 9/0.5/0.1): Rf lower than that of the starting product obtained in example A (UV detector). Melting point is 213°-215° C.

EXAMPLE D

N-(2-mercaptoethyl)-N'-(3,4-methylenedioxybenzyl)-2-nitro-1,1-ethenediamine

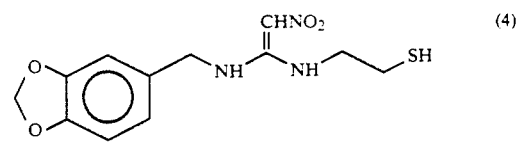

In a 100 ml 4-necked flask under a nitrogen atmosphere are placed methanol (25 ml), water (5 ml) and 5.5 g of the product obtained in example (C).

1.05 g of $NaBH_4$ are added slowly in small portions. Hydrogen is developed intensely and regularly. At the end of the addition stirring is continued at 45°-50° C. for 18 hours. The heterogeneous yellow reaction mixture is poured into water. The precipitate formed is filtered and placed in an oven to dry. 4.8 g of product are obtained with a yield of 87.8%. TLC control (Merck 5554; eluent: ethyl acetate/methanol/$H_2O$ 9/0.5/0.1).

Detector: cerium phosphomolybdate. The product (4) becomes pale blue.

Melting point is 236°-238° C.

EXAMPLE E

N-[2-[[[5-[(dimethylamino)-methyl]-2-furanyl]methyl]thio]ethyl]-N'-(3,4-methylenedioxybenzyl)-2-nitro-1,1-ethylenediamine (niperotidine)

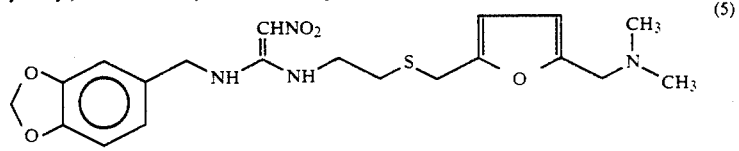

In a 100 ml 3-necked flask equipped with a thermometer and mechanical stirring are placed 20 ml of dimethylformamide to which are added 0.5 g of NaOH in a nitrogen atmosphere. After 10 minutes of stirring at room temperature 4 g of the product obtained in example D divided in four 1 g portions are added at 15-minutes intervals. At the end of the addition the mixture is stirred at room temperature for approximately 1 hour. Then 3.38 g of 5-dimethylaminomethyl furfuryl chloride separately freed from the hydrochloride with 0.53 g of NaH in dimethylformamide (20 ml) are added. At the end of the addition the mixture is heated to 70°–75° C. for 1 hour, then cooled to room temperature. The reaction mixture is concentrated to a small volume. The residue is purified by partitioning between 50 ml of water and 50 ml of chloroform to eliminate the salts. The chloroform phase is filtered, made anhydrous (anhydrous $Na_2SO_4$) and concentrated to dryness. An oily substance (4.8 g) is obtained which is dissolved in 15 g of ethylacetate and held below 0° C. A crystalline precipitate (3 g) is formed with 51% yield. Melting point: 113°–115° C. TLC control (Merck 5554, eluent: ethyl acetate/methanol/NaOH 9/0.5/0.2; detector; iodine or cerium phosphololybdate). Rf=0.2 The IR spectrum (KBr) of the final product corresponds to the reference compound.

I claim:

1. A process for the preparation of compounds of the formula:

$$Ar-CH_2-S-(CH_2)_n-NH-\overset{\overset{X}{\|}}{C}-NH-R_1 \qquad (V)$$

wherein $R_1$ is selected from the group consisting of hydrogen, alkyl and,

[structure: methylenedioxyphenyl-CH2 group]

Ar is selected from the group consisting of

[structure: (CH3)2N-CH2-furan ring with CH2 substituent]

and

[structure: methylisoxazole/pyrazole ring with CH3 substituent, N and NH]

$n=1, 2, 3, 4, 5,$ or 6 and X represents $CH-NO_2$ or $N-C\equiv N$, said process comprising:

a) reacting a carbamate of the formula:

$$R_1-NH-\overset{\overset{O}{\|}}{C}-O-\text{[phenyl]}-Z \qquad (VIII)$$

with $Z = H$, halogen, $NO_2$ wherein Z is H, halogen or $NO_2$ with a bisdithio-alkylamine of the formula:

$$H_2N-(CH_2)_n-S-S-(CH_2)_n-NH_2 \qquad (IX)$$

to obtain a urea of the formula:

$$R_1-NH-\overset{\overset{O}{\|}}{C}-NH-(CH_2)_n-S-S-(CH_2)_n-NH-\overset{\overset{O}{\|}}{C}-NH-R_1 \qquad (I)$$

wherein $R_1$ and n have the meaning recited above;

b) reacting the urea of formula (I) with a compound capable of converting the compound of formula (I) into the corresponding biscarbodiimide of the formula:

$$R_1-N=C=N-(CH_2)_n-S-S-(CH_2)_n-N=C=N-R_1 \qquad (II)$$

c) reacting the carbodiimide of formula (II) with a compound selected from the group consisting of nitromethane and a saline derivative of cyanamide to form a product of the formula:

$$R_1NH-\overset{\overset{X}{\|}}{C}-NH-(CH_2)_n-S-S-(CH_2)_n-NH-\overset{\overset{X}{\|}}{C}-NH-R_1 \qquad (III)$$

wherein X is $CH-NO_2$ or $N-C\equiv N$, said nitromethane is used in the presence of a strong base.

d) reacting the compound of formula (III) with a compound which reduces the $-S-S-$ group to obtain a compound of formula:

$$R_1-NH-\overset{\overset{X}{\|}}{C}-NH-(CH_2)_n-SH; \text{ and} \qquad (IV)$$

e) reacting the compound of formula (IV) with a reactant of the formula $Ar-CH_2-Cl$ to obtain the desired product of formula (V).

2. Process in accordance with claim 1, characterized in that stage (a) is carried out at a temperature of 40°–50° C. in a solvent capable of solubilizing the urea (I).

3. Process in accordance with claim 1, characterized in that said bis-dithio-alkylamine (IX) is in the form of its hydrochloride salt and is freed from its hydrochloride by treatment with an aqueuous soda solution.

4. Process in accordance with claim 2 characterized in that said solvent must be at least partially miscible with water.

5. Process in accordance with claim 2 characterized in that said solvent is pyridine.

6. Process in accordance with claim 1 characterized in that said compound capable of converting the urea (I) into the corresponding bis-carbodiimide (II) is selected from among triphenylphosphine, sulfuryl chloride and thionyl chloride.

7. Process in accordance with claim 6 characterized in that in the case of triphenylphosphine bromine is present also.

8. Process in accordance with claim 6 characterized in that the conversion of urea (I) into the corresponding bis-carbodiimide (II) takes place in the presence of an acid acceptor.

9. Process in accordance with claim 8 characterized in that said acid acceptor is an organic base.

10. Process in accordance with claim 9 characterized in that said organic base is triethylamine.

11. Process in accordance with claim 6 characterized in that the conversion of urea (I) into the corresponding bis-carbodiimide (II) is carried out in an aprotic solvent.

12. Process in accordnace with claim 11 characterized in that said aprotic solvent is a chlorinated hydrocarbon.

13. Process in accordance with claim 12 characterized in that said chlorinated hydrocarbon is selected from between dichloromethane and chloroform.

14. Process in accordance with claim 6 characterized in that the conversion of urea (I) into the corresponding bis-carbodiimide (II) is carried out at low temperature.

15. Process in accordance with claim 6 characterized in that the urea (I) is introduced in a reactant prepared from (a) a compound selected from the group consisting of triphenylphosphine, thionyl chloride and sulfuryl chloride dissolved in a reaction solvent, (b) an acid acceptor and optionally (c) bromine.

16. Process in accordance with claim 15 characterized in that said reactant is present in excess of the urea (I).

17. Process in accordance with claim 1 characterized in that when X is $CH-NO_2$ in stage (c) the reaction is carried out in a polar aprotic solvent.

18. Process in accordance with claim 17 characterized in that said aprotic solvent is dipolar.

19. Process in accordance with claim 18 characterized in that said dipolar aprotic solvent is selected from among dimethylformamide and dimethylsulfoxide.

20. Process in accordance with claim 17 characterized in that said nitromethane is present in a molar excess of the carbodiimide (II).

21. Process in accordance with claim 17 characterized in that the reaction is carried out at approximately 40° C. for 15 to 20 hours.

22. Process in accordance with claim 17 characterized in that the strong base added to the nitromethane is sodium hydride.

23. Process in accordance with claim 1 characterized in that when X is $N-C\equiv N$ in stage (c) the reaction is carried out with the sodium salt of the cynamide.

24. Process in accordance with claim 1 characterized in that said stage (d) is carried out in a mixture of water and alcohol as solvent.

25. Process in accordance with claim 24 characterized in that said alcohol is methanol and is present in excess of the water present forming the reaction solvent.

26. Process in accordance with claim 1 characterized in that said last stage (e) is carried out in a polar aprotic solvent.

27. Process in accordance with claim 26 characterized in that said aprotic solvent is dipolar.

28. Process in accordance with claim 27 characterized in that said dipolar aprotic solvent is selected from among dimethylformamide and dimethylsulfoxide.

29. Process in accordance with claim 1 characterized in that said stage (e) is performed at 70°-80° C.

* * * * *